United States Patent [19]
Spallholz et al.

[11] Patent Number: 5,994,151
[45] Date of Patent: Nov. 30, 1999

[54] SELENIUM CARRIER CONJUGATES

[75] Inventors: Julian E. Spallholz; Ted W. Reid, both of Lubbock, Tex.

[73] Assignee: Richard-James, Inc., Peabody, Mass.

[21] Appl. No.: 09/012,161

[22] Filed: Jan. 22, 1998

Related U.S. Application Data

[60] Division of application No. 08/432,584, May 9, 1995, Pat. No. 5,783,454, which is a continuation-in-part of application No. 08/243,704, May 17, 1994, abandoned.

[51] Int. Cl.⁶ ................................. G01N 33/533
[52] U.S. Cl. .................. 436/525; 424/1.29; 424/1.49; 424/1.53; 424/417; 424/420; 424/422; 424/432; 424/428; 424/489; 424/490; 424/181.1; 427/2.14; 604/890.1; 604/891.1; 604/4; 604/5; 604/6
[58] Field of Search ................... 424/1.29, 1.49, 424/1.53, 417, 420, 422, 423, 428, 489, 490, 181.1; 427/2.14; 604/890.1, 89.1, 4–6; 436/525

[56] References Cited

U.S. PATENT DOCUMENTS

| | | |
|---|---|---|
| 4,166,820 | 9/1979 | Spallholz . |
| 4,341,757 | 7/1982 | Spallholz . |
| 4,584,277 | 4/1986 | Spallholz . |
| 4,671,958 | 6/1987 | Rodwell et al. . |
| 4,937,183 | 6/1990 | Ultee et al. . |
| 5,057,313 | 10/1991 | Shih et al. . |
| 5,104,852 | 4/1992 | Kralick et al. . |
| 5,225,182 | 7/1993 | Sharma . |

FOREIGN PATENT DOCUMENTS

| | | |
|---|---|---|
| 0 140 538 | 5/1985 | European Pat. Off. . |
| WO91 08775 | 6/1991 | WIPO . |
| WO93 17692 | 9/1993 | WIPO . |
| WO94 00135 | 1/1994 | WIPO . |

OTHER PUBLICATIONS

Biochem. Pharmacol., vol. 1 45, No. 2, Jan. 26, 1993, pp. 429–437, Yan L. et al. "Generation of Reactive Oxygen Species from the Reaction of Selenium Compounds with Thiols and Mammary Tumor Cells." See p. 429, col. 2.

Chemical Abstracts. vol. 112, No. 17, Apr. 23, 1990, Columbus, Ohio, US; abstract No. 151194, Nomura, H. et al. "Binding of ebselen to plasma protein" see Abstract & Selenium Biol. Med., [Proc. Int. Symp.], 4$^{th}$ (1989), Meeting Date 1988, 189–93. Editor(s): Wendel,Albrecht. Publisher: Springer, Berlin, Fed. Rep. Ger. Coden 56Ssmat, 1989.

Chemical Abstracts, vol. 120, No. 21, May 23, 1994, Columbus, OH US; abstract No. 260711, Shenberg, Cesia et al "An XRF study of trace elements accumulation in kidneys of tumor–bearing mice after treatent with cis–DDP with the without selemnite ans selenocystamie" see abstract & Biol. Trace Elem. Res. (1994), 40(2), 137–49 Coden: BTERDG; ISSN: 0163–4984, 1994.

Chemical Abstracts, vol. 115, No. 17, Oct. 28, 1991, Columbus, OH, US; abstract No. 181934; Yan Lin et al "Effect of selenium compounds and thiols on human mammary tumor cels" see abstract & Biol. Trace Elem. Res/ (1991), 30(2), 145–62 Coden: BTERDG: ISSN: 0163–4984, 1991.

Biochemistry, vol. 10, No. 22, p. 4089 et seq., 1971, Reduction of the Delentrisulfide Derivative of Glutathione to a Persulfide Analog by Glutathione Reductase, Howard E. Ganther.

*Primary Examiner*—Christopher L. Chin
*Assistant Examiner*—Bao-Thuy L. Nguyen
*Attorney, Agent, or Firm*—Kirkpatrick & Lockhart LLP

[57] ABSTRACT

The invention provides a method for making a selenium-carrier conjugate by covalently attaching (i) an organic selenium compound selected from the group consisting of RSeH, RSeR, RSeR', RSeSeR and RSeSeR', wherein R and R' are each an aliphatic residue containing at least one reactive group selected from the group consisting of aldehyde, amino, alcoholic, carboxylic, phosphate, sulfate, halogen or phenolic reactive groups and combinations thereof, to (ii) a carrier having a constituent capable of forming a covalent bond with said reactive groups of said selenium compound to produce a selenium-carrier conjugate which is capable of specific attachment to a target site. The carrier may be a protein, such as an antibody specific to a bacteria, virus, protozoa, or cell antigen, including without limitation, cell surface antigens, a peptide, carbohydrate, lipid, vitamin, drug, lectin, plasmid, liposome, nucleic acid or a non-metallic implantable device, such as an intraocular implant or a vascular shunt. The attachment of selenium compounds of the configurations described above to carriers when presented to either endogenous thiols, such as glutathione which occurs in all aerobic living cells, or exogenous thiols, such as glutathione or cysteine, produces superoxide ($O_2.^-$), hydrogen peroxide, the hydroxyl radical (.OH) and other cytotoxic reactive oxygen species so as to collectively form a localized free radical pharmacology based upon the catalytic selenium anion, $RSe^-$.

3 Claims, 5 Drawing Sheets

SELENIUM CARRIER CONJUGATES

This application is a divisional of application Ser. No. 08/432,584 filed May 9, 1995 now U.S. Pat. No. 5,783,454, which is a continuation-in-part of application Ser. No. 08/243,704, filed May 17, 1994, now abandoned.

BACKGROUND OF THE INVENTION

1. Field of the Invention

The present invention relates to selenium compounds, and more specifically to selenium compounds which, when covalently attached to functional and site directed molecules and devices, produce superoxide and other reactive compounds in the presence of thiols.

2. Description of the Invention Background

Selenium (Se) is among the most toxic of all known minerals. Its toxicity symptoms in horses were most likely described by Marco Polo while traveling the silk road in China. In the 1920's, loss of livestock in parts of the western and central United States was severe. Those losses of livestock were investigated by the United States Department of Agriculture Experiment Station in South Dakota. In 1934, the cause of the loss of livestock was traced by the Experiment Station to the element selenium which was high in certain soils and high secondarily in plants from several species of Astragalus (vetch), Xylorrhiza (woody aster), conopsis (goldenrod) and Stanleya (Prince's Plume). Ingestion of these and other Se containing plants by livestock often proved to be fatal.

Throughout the period of time between the discovery of selenium toxicity in livestock in 1934 and 1988, many hypotheses were put forth to explain the mechanism by which many but not all compounds of selenium were toxic. None of these theories of selenium toxicity proved satisfactory in fully explaining why selenium was toxic. In 1989, Seko, Y. E., Saito, Y. Kitahare, J. and Imura, N., "Active oxygen generation by the reaction of Selenite with reduced glutathione in vitro," In: *Proceedings of the fourth international symposium on selenium and medicine* (ed., Wendel, A.) pp. 70–73, Springer-Verlag, Heidelberg, Germany, (1989), reported that selenite, ($SeO_3$), an inorganic form of Se, reacted with a thiol, glutathione, (GSH), to produce superoxide ($O_2.^-$). Since superoxide is a known toxicant, this raised the possibility that all selenium compounds that are toxic might generate superoxide. Through the testing of many selenium compounds, it was found that the inorganic compounds, $SeO_3$ and selenium dioxide ($SeO_2$) were able to generate $O_2.^-$ and hydrogen peroxide ($H_2O_2$) when presented with a thiol, such as glutathione, cysteine (CysSH), or dithiothreitol D(SH)$_2$. Furthermore, it was found that all diselenides of the composition RSeSeR tested likewise would generate $O_2.^-$ and $H_2O_2$ when presented with any of the before mentioned thiols.

In 1947, Feigl, F. and West, P. W. "Test for selenium based on a catalytic effect", *Analytical Chemistry*, vol. 19, pp. 351–353 (1947), reported that selenium could catalyze a redox reaction involving sulfide oxidation. This soon became a common test for selenium using methylene blue. This reaction was further studied by others using different selenium compounds and thiols, demonstrating catalysis for some but not all selenium compounds. See, West, P. W. and Ramakrishna, T. V. "A catalytic method for determining traces of selenium," *Analytic Chemistry*, vol. 40, pp. 966–968 (1968); Levander, O. A., Morris V. C., and Higgs, D. J. "Selenium as a catalyst for the reduction of cytochrome C by glutathione", *Biochemistry*, vol. 12, pp. 4591–4595 (1973), Rhead, N. J. and Schrauzer, G. N., "The selenium catalyzed reduction of methylene blue by thiols", *Biorganic Chemistry*, vol. 3, pp. 225–242 (1974). The selenium catalytic activity of selenocystine (RSeSeR) in the presence of thiols was reported in 1958. It is now believed that all of the foregoing reactions of selenium compounds produce superoxide. See, Xu, M., Zhang, L., Sun, E. and Fan, H., "Studies on the interaction of trace element selenium with oxygen free radical," *Advances in Free Radical Biology and Medicine*, vol. 1, pp. 35–48 (1991); Xu, H., Feng, Z., and Yi, C., "Free radical mechanism of the toxicity of selenium compounds," *Huzahong Longong Daxus Xuebao*, vol. 19, pp. 13–19 (1991); Kitahara, J., Seko, Y. and Imura, N., "Possible involvement of active oxygen species in selenite toxicity in isolated rat hepatocytes," *Archives of toxicology*, vol. 67, pp. 497–501 (1993); Chaudiere, J., Courtin, O. and Ledaire, J., "Glutathione oxidase activity of selenocystamine: a mechanistic study," *Archives of Biochemistry and Biophysics*, vol. 296, pp. 328–336 (1992).

Selenium and a number of its compounds have been known since the early 1970's to possess anti-cancer properties. It has been generally recognized that selenite and selenium dioxide are good anti-cancer agents in vitro and in experimental animals and that the compounds are also cytotoxic to both cancer and normal cells in vitro. U.S. Pat. No. 5,104,852 to Kralick et al. describes the use of selenodiglutathione and other selenodithiols of the configuration (GSSeSG) to treat cancer. Selenodiglutathione is the product of the reaction between selenite or selenium dioxide with glutathione. The compound, selenodiglutathione, has been isolated. U.S. Pat. No. 5,104,852, however, does not describe the mechanism of action by which selenodiglutathione and like compounds are useful in treating cancer.

In 1982, the interaction of selenite and selenocystine with glutathione in the cytotoxicity and lysis of rat erythrocyte membranes was described by Hu, M. L. and Spallholz, J. E., "In vitro hemolysis of rat erythrocytes by selenium compounds", *Biochemical Pharmacology*, vol. 32, pp. 857–961 (1983). This cytotoxicity, as revealed by scanning electron microscopy of rat erythrocytes, caused the erythrocyte membranes to become burred, the cells to quadruple in size and lyse similar to that described by Kellogg, E. and Fridovich, I., "Liposome oxidation and erythrocyte lysis by enzymically generated superoxide and hydrogen peroxide," *J. Biol. Chem.*, vol. 252, pp. 6721–6728 (1977). This toxicity, however, was not expressed by selenomethionine, a compound possessing the configuration RSeR. In 1991, an article by Yan, L. and Spallholz, J. E., "Free radical generation by selenium compounds," FASEB J., vol. 5, p.A581 (1991), showed a dose responsive toxicity of several selenium compounds to a human mammary tumor cell line. Additional investigations using lucigenin chemiluminescence and luminol chemiluminescence revealed a dose response in $O_2.^-$ and $H_2O_2$ generated chemiluminescence by selenite, selenium dioxide and all selenium compounds tested of the configuration RSeSeR. It was found furthermore, that selenium compounds in the presence of either tumor cells or glutathione alone produced superoxide and $H_2O_2$. Chemiluminescence from the reactions of lucigenin with $O_2.^-$ or luminol with $H_2O_2$ could be quenched by the native enzymes superoxide dismutase (SOD), catalase (CT) or glutathione peroxidase (GSHPx). Denatured enzymes would not quench these reactions, confirming the generation of the free radical ($O_2.^-$) and $H_2O_2$ by selenium compounds and thiols. All of this selenium free radical chemistry has been reviewed by Spallholz, J. E., "On the nature of selenium toxicity and carcinostatic activity," *Free Radical Biology and Medicine*, vol. 17, pp. 45–64, (1994).

A summation of this large body of experimental data on selenium toxicity, catalysis and carcinostatic activity is as follows:

1) The selenium compounds, $SeO_2$ and $SeO_3$, react with thiols to produce a selenodithiol of the configuration (RSSeSR). This compound is not toxic per se nor is it carcinostatic. The toxic carcinostatic form of RSeR is the reduced selenide anion, $RSe^-$. This selenopersulfide form of Se is catalytic as shown by the inhibition of both catalysis and superoxide generation by iodoacetic acid and mercaptosuccinic acid.

2) Selenium compounds of the configuration (RSeSeR) or (RSeSeR') react with thiols to produce the reduced selenite anion $RSe^-$ or $R'Se^-$. This selenopersulfide form of Se is catalytic as shown by the inhibition of both catalysis and superoxide generation by iodoacetic acid and mercaptosuccinic acid.

3) Organic selenium catalysts by the configuration $RSe^-$ the selenopersulfide anion, is catalytic in the presence of thiols and $RSe^-$ continues to generate superoxide $(O_2.^-)$ ion as long as sufficient concentrations of $O_2.^-$ and thiol are in the medium. Selenium compounds derived from selenite or selenium dioxide reacting with glutathione (GSH) are converted to elemental selenium (Se) follows; $SeO_3$ $(SeO_2)$+2GSH-2GSSeSG-2GSSG+ Se. Elemental selenium (Se) is non-catalytic and not toxic.

4) Compounds of selenium of the configuration $RSe^-$ are toxic due to the catalytic acceleration of thiol oxidation which produces $O_2.^-$, $H_2O_2$ and the more toxic free radical, the hydroxyl radical (.OH). This chemistry had been discussed by Misra, H. P., "Generation of superoxide free radical during the auto-oxidation of thiols," *J. Biol. Chem.*, vol. 249, pp. 2151–2155 (1974) for the spontaneous oxidation of thiols. The association of rapid thiol catalysis by selenium compounds of the configuration $RSe^-$ and the toxicity from which it produced free radicals and reactive toxic oxygen products was recognized in 1992 by one of the inventors.

The use of selenium for the treatment of experimental cancer in animals and cancer in humans in vivo has been extensively described by many authors, such as Milner, J. A., Greeder, G. A., Poirier, K. A., "Selenium and transplantable tumors," (Spallholz, J. E., Martin, J. L., Ganther, H. E., eds.) *Selenium in Biology and Medicine*, AVI Publishing Co. (1981); Ip, C. and Ganther, J. E., "Relationship between the chemical form of selenium and anticarcinogenic activity," *CRC Press, Inc.*, pp. 479–488 (1992); Caffrey, P. B. and Frenkel, G. D. "Selenite cytotoxicity in drug resistant and nonresistant human ovarian tumor cells," *Cancer Research*, vol. 52, pp. 4812–4816 (1992); Schrauzer, G. N., "Selenium: Mechanistic aspects of anticarcinogen action", *Biol. Trace Elem. Res.*, vol. 33, pp. 51–62 (1992); Yan, L. and Spallholz, J. E. "Generation of reactive oxygen species from the reaction of selenium compounds with thiols and mammary tumor cells," *Biochemical Pharmacology*, vol. 45, pp. 429–437 (1993). The use of selenium as a cytotoxic agent to both normal cells and cancer cells in vitro has been described in U.S. Pat. No. 5,104,852 for the injection of selenodiglutathione into a tumor mass to kill tumor cells. In U.S. Pat. No. 4,671,958, Rodwell et al. described many antibacterial drugs, 3 antiviral drugs, 1 antifungal drug, 7 antineoplastic drugs, 3 radiopharmaceuticals, 3 heavy metals and 2 antimycoplasmals as drugs for antibody mediated delivery. The pharmacology for all of these drugs which are listed in Table 1 of U.S. Pat. No. 4,671,958 is generally understood. Table 1 of the Rodwell et al. patent does not contain selenium because its pharmacological action as a free radical generator of $(O_2.^-)$ and other reactive oxygen molecules was not understood or known at that time.

Viral infections are difficult to treat because viruses lack an uptake mechanism by which agents designed to kill or damage the virus can be taken into the virus. Even when it is known that a person has been infected with a virus, it has been necessary heretofore to wait for the virus to infect cells in the host and reproduce in the cells. The cell, which does have an uptake mechanism, will takeup the agent. Viral reproduction can only then be blocked. In practice, the viral infection has usually spread by the time treatment is possible. This is particularly devastating with HIV viral infections, the causative agent for acquired immune deficiency syndrome (AIDS). Often, an infected person knows that he or she has been exposed to the virus but is unable to stop the spread of the virus until that person's cells have been infected.

Once-reliable antibiotics for treating bacterial infections are falling by the way side. With the emergence of many conventional drug-resistant strains of bacteria, such as those identified in the Mar. 28, 1994 issue of Newsweek magazine and set forth below in Table 1, the need for a new agent for combating infectious diseases is becoming critical.

TABLE 1

DRUG RESISTANT BACTERIA

| BACTERIA | DISEASES CAUSED | ANTIBIOTICS THAT NO LONGER WORK |
|---|---|---|
| Enterococcus | Blood poisoning, surgical infections | Aminoglycosides, cephalosporins, erythromycin, penicillin, tetracycline, vancomycin |
| Hemophilus influenza | Meningitis, ear infections, pneumonia, sinusitis | Chloramphenicol, penicillins, tetracycline, trimethorprirm/ sulfamethoxazola |
| Mycobacterium tuberculosis | Tuberculosis | Aminoglycosides, ethambuto1, isoniazid, pyrazinamide, rifampin |
| Neisseria gonorrhea | Gonorrhea | Penicillins, spectinomycin, tetracycline |
| Plasmodium falciparurn | Malaria | Chloroquine |
| Shigella dysenteriae | Severe Diarrhea | Ampicillin, chloramphenicol, tetracycline, trimethoprim/ sulfamethoxazole |
| Staphylococcus aureus | Blood poisoning, pneumonia, surgical infections | All but Vancomycin |
| Streptococcus pneumoniae | Meningitis, pneumonia | Aminoglycosides, cephalosporins, chloramphenicol, crythromycin, penicillins, tetracycline, trimethorprim/ sulfamethoxazola |

It is an object of the invention to provide a new bacterialcidal and viralcidal agent.

It is a further object of this invention to provide a methodology to use of the aforementioned free radical technology as bacterialcidal or viralcidal agents. It is a further object of the present invention to provide a method for directing the localized production of superoxide and descendant species thereof for selective destruction or modification of cells, tissue, membranes or extraceluler fluids to combat a variety of localized problems, from infections, to cancer, to post surgical clotting and fibrosis.

SUMMARY OF THE INVENTION

The present invention comprises the organic covalent chemical attachment of organic selenium compounds of the configuration, RSeH, RSeR, RSeR',RSeSeR or RSeSeR' to various carrier molecules, where R and R' are each selected from the group consisting of aliphatic residues containing one or more aldehyde, carboxylic, amino, alcoholic, phosphate, sulfate, halogen or phenolic reactive groups, and combinations thereof, such as $—(CH_2)_nHN_2$, $—(CH_2)_nCOOH$, $—(CH_2)_n—Ø$, wherein n is an integer equal to or greater than 1. R and R' can be the same or different. The carrier molecules, which have a complementary reactive constituent capable of forming a covalent bond with the reactive groups of the selenium compound, include monoclonal antibodies, polyclonal antibodies, polypeptides, peptides, carbohydrates, lipids, vitamins, drugs and other organic carriers or devices for the treatment of diseases caused by pathogens, such as viral, bacterial, protozoan, richetcial, yeast, mycoplasma, fungi or other pathogens and diseases of either known or unknown etiology, such as cancers and glaucoma. The present invention is directed to the treatment and cure of a wide spectrum of cancers, bacterial, viral and other biotic infections.

An interesting discovery of the invention is that the tissue, cell or bodily fluid provides the reducing power for the generation of superoxide ($O_2.^-$). However, should additional reducing power be needed in vivo it can be supplied by exogenous glutathione or cysteine according to known techniques.

The invention also includes a method for treating cancer tumors and pathogenic infections by means of administering an effective amount of a selenium-carrier conjugate for localized delivery and attachment to a target site comprising cancer tumors and pathogens having endogenous thiol compounds. The selenium-carrier conjugate comprises (i) an organic selenium compound selected from the group consisting of RSeH, RSeR, RSeR',RSeSeR and RSeSeR', wherein R and R' are the same or different and each is an aliphatic residue containing at least one reactive group selected from the group consisting of aldehyde, amino, alcoholic, carboxylic, phosphate, sulfate, halogen or phenolic reactive groups and combinations thereof, covalently attached to (ii) a carrier having a constituent capable of forming a covalent bond with the reactive groups of the selenium compound to produce the selenium-carrier conjugate. The carrier is capable of specific attachment to the target site for the localized generation of superoxide for localized destruction at the target site. The invention also includes a method for preventing tissue damage associated with the use of implants and the prevention of unwanted scarring in surgical procedures. The aforementioned organic selenium compound is covalently attached to the surface of an implantable device or a stationary matrix, resulting in a selenium-coated device or carrier, as the case may be, for the localized generation of superoxide at the implant, or surgical site to inhibit the formation of scar tissue or other undesirable cellular growth.

The invention also comprises the attachment of these same selenium adducts for immunoassays and other quantitative analytical work as described by U.S. Pat. No. 4,341,757, dated Jul. 23, 1982 which is incorporated herein by reference. The invention includes, for example, a method for detecting the presence of a compound of biological interest comprising the steps of incubating together a mixture of a sample suspected of containing a compound of biological interest and a selenium-carrier conjugate as described above, wherein the carrier is capable of specific attachment to the compound of biological interest, to bind the selenium-carrier conjugate to a determinant on the compound of biological interest. Then, any unbound selenium-carrier conjugate is removed. Thereafter, the method includes the steps of adding a thiol compound to the mixture to react with the selenium to generate superoxide, then adding a reporting agent to the mixture. The reporting agent is capable of reacting with superoxide. Finally, the reaction between the reporting agent and superoxide is detected. The reporting agent may be, for example, lucigenin, methylene blue or cytochrome C. Compounds of biological interest may be proteins, vitamins, hormones, enzymes, antibodies, polysaccharides, cell and tissue antigens, the pathogens described herein, drugs or other blood cell or intra or extracellular fluids. Antibodies specific to any of those compounds can be made by well known techniques. Such antibodies can be used as the carrier for attachment to the selenium compound of the invention.

The attachment of selenium compounds of the configurations described above to carriers, diagnostics or devices when presented to either endogenous thiols, such as glutathione which occurs in all aerobic living cells, or exogenous thiols, such as glutathione or cysteine, produces superoxide ($O_2.^-$), hydrogen peroxide, the hydroxyl radical (.OH) and other cytotoxic reactive oxygen species so as to collectively form a localized free radical pharmacology and new pharmacopeia based upon the catalytic selenium anion, $RSe^-$ Because superoxides are so deadly to cells, the body has natural mechanisms to destroy the superoxides, i.e., with dismutase. Thus, the superoxide radical, $O_2.^-$, has a relatively short half life and will degrade. $H_2O_2$ and OH are secondarily produced and are slightly longer lived. As used herein, for brevity, superoxide will include $O_2.^-$ and its descendent oxygen species. Because of the short life, $O_2.^-$ must be generated at or near the site of intended destruction. The covalent attachment of selenium compounds which produce the $RSe^-$ anion provide for a new analytical chemistry based upon the generation and detection of superoxide ($O_2.^-$) using chemiluminescence or the reduction of various dyes, such as methylene blue or cytochrome C. Methylene blue and cytochrome C in the oxidized form may be reduced by selenium attached to a receptor molecule, through the generation of superoxide. The amount of reduced methylene blue or cytochrome C can be measured spectrophotometrically and quantitated, thereby reflecting the concentration of the molecule to which selenium is attached.

This invention provides preferably for a small molecular adduct, RSeH, RSeR, RSeR', RSeSeR or RSeSeR', the detector group for analytical chemistries using chemiluminescence or chemical dyes by producing superoxide ($O_2.^-$); and the generator of superoxide ($O_2.^-$) whereby it is only toxic in a very localized area produced by the conjugate $RSe^-$ and which is determined by the binding of a carrier molecule or localized by a stable insoluble matrix. The present invention substantially overcomes the generalized problem of systemic selenium toxicity in the treatment of diseases such as metastatic cancer and demonstrates a new applied free radical pharmacology. This invention represents a major advancement in the application of selenium toxicity in the treatment of diseases and in the extension or analytical sensitivity and ease of detection for stable isotopic immunoassays. The targeting superoxide free radical pharmacology, based upon the addition of selenium to targeting molecules of the present invention holds promise for a new bacterial pharmacopeia. The same is also true for viral infections whereby conjugation of the appropriate selenium configuration to a viral targeting agent, such an antibody or binding peptide will render a virulent virus non-virulent.

BRIEF DESCRIPTION OF THE DRAWINGS

The invention can be better understood by reference to the figures in which.

DETAILED DESCRIPTION OF THE PREFERRED EMBODIMENTS

Figure 1:
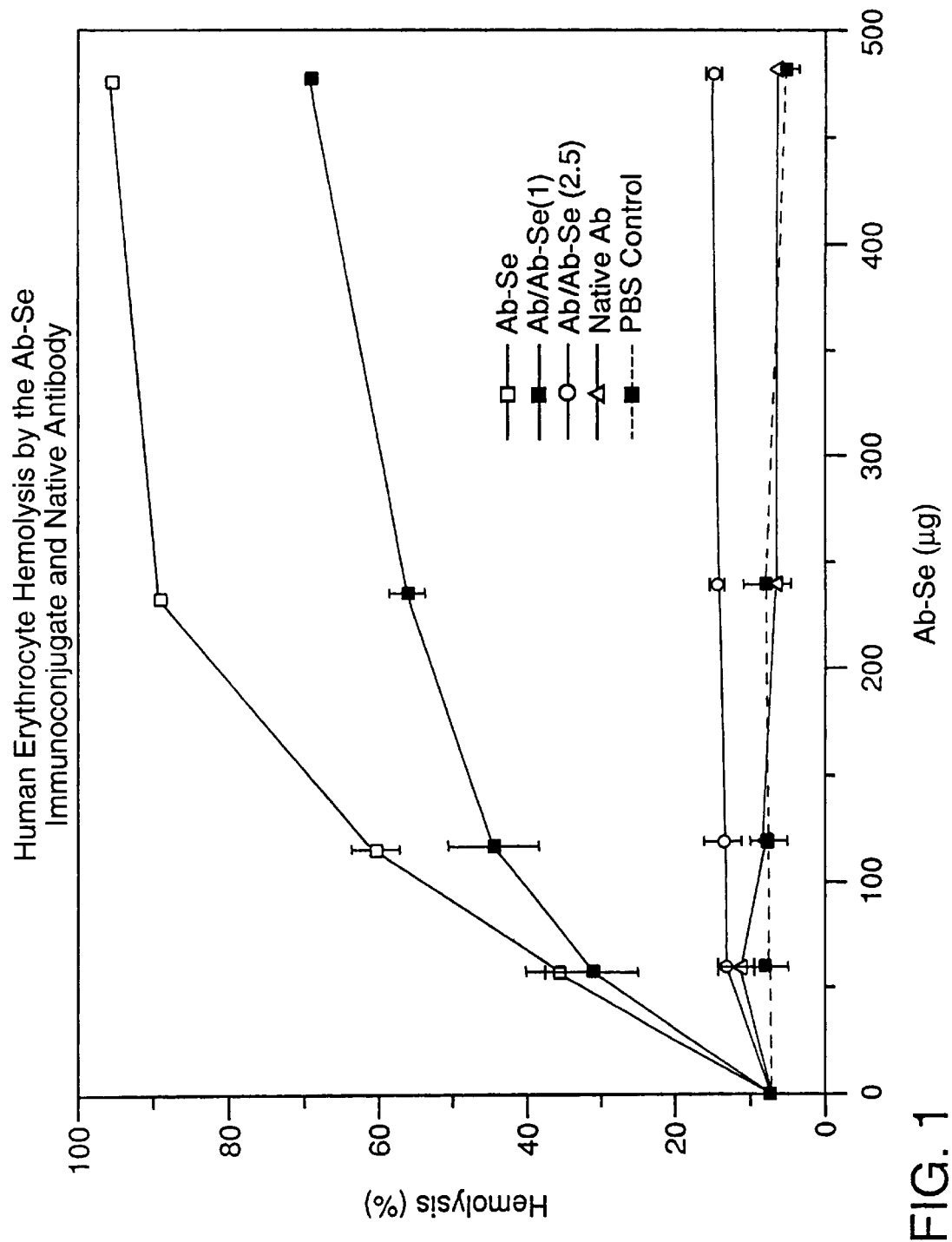
FIG. 1 is a graph demonstrating the percent hemolysis of human erythrocytes produced by Ab-Se conjugates, native Ab, and combinations of the two.

This invention relates to the covalent attachment of selenium adducts of the configuration RSeH, RSeR, RSeR', RSeSeR or RSeSeR' to carrier molecules, diagnostics and devices. The Se-carrier conjugate thus produced is administered by injection or ingestion and carried by normal physiologic means to a target site or target molecule, or surgically implanted at a target site, whereupon superoxide ($O_2.^-$) is generated when the Se-carrier conjugate reacts with endogenous thiols on the surface of the targeted local tissue, bacteria, virus, protozoa or other targeted compounds. The selenium toxicity produced by the conjugate RSe$^-$ is very localized because it is determined by the specific binding of the carrier molecule or localized by the stable insoluble matrix of an implant. R and R' are each selected from the group consisting of aliphatic residues containing one or more aldehyde, carboxylic, amino, alcoholic, phosphate, sulfate, halogen or phenolic reactive groups, and combinations thereof, such as —$(CH_2)_n HN_2$, —$(CH_2)_n COOH$, —$(CH_2)_n$—Ø, wherein n is an integer greater than 1, and preferably between about 1 and 50, and more preferably between about 3 to 5. R and R' can be the same or different. The R groups themselves have no real role in the method of the invention, other than to provide reactive groups to bind to the carrier and to protect the selenium until it reaches the target sites. Accordingly, the length of the aliphatic chain is not important. The preferred molecule weight of the compound is about 1000 or less, but higher MWs will be suitable. Representative examples of selenium compounds include, but are not limited to $NH_2CH_2CH_2SeCH_3$ (RSeR'), $NH_2CH_2CH_2SeCH_2CH_2NH_2$ (RSeR), $NH_2CH_2CH_2SeSeCH_2CH_2NH_2$ (RSeSeR), $NH_2CH_2CH_2SeSeCH_2CH_2NH$-cellulose (RSeSeR') and selenocystamine. The RSeH, RSeSeR, and RSeSeR' configurations are preferred. These selenium compounds are covalently or otherwise attached to any polyclonal or monoclonal antibody which, when brought into contact with thiol, can then generate superoxide ($O_2.^-$), $H_2O_2$, or hydroxyl radical (.OH) or any other reactive oxygen specie. The thiols can be exogenous thiols added for example, to a competitive immunoassay, endogenous thiols found in membranes, cellular cytoplasm or extracellular fluids. If native thiols are insufficient, exogenously supplied glutathione, glutathione derivatives, cysteine or other thiol can be used expressly for the generation of superoxide. The selenium-carrier conjugate is used to treat, in a pharmacological manner, cancer, both primary and metastatic, infections and diseases caused by all viruses of all plant, animal or human origin, all bacteria of all plant, animal or human origin, all protozoans of all plant, animal or human origin and other pathogens. The antibody-selenium conjugate, for example, will specifically bind to the virus, bacteria, protozoa or cancer cells and catalyze the production of superoxide, $H_2O_2$ and other reactive oxygen species. Viruses have surface proteins to which the antibody selenium-conjugate can attach. The selenium reacts with thiols in those surface proteins to generate the superoxide on the surface of the virus. The lack of an uptake mechanism in the virus is not important because the damage is done at the viral surface.

When the organic Se compound is attached to a site directed antibody molecule, it is believed to typically bind at the F(Ab$^-$)2 fragment of the antibody. Other fragments of the antibody, natural or synthetic, can be the site of attachment, such as carbohydrates or modified amino acids.

The site directing molecule that carries selenium can be any protein, polypeptide, peptide, carbohydrate, lipid, drug, vitamin, hormone, lectin, plasmid, liposome, nucleic acids, or other site directed organic molecules for which their exists a receptor. Such site directed substances are known to those skilled in the art. Whatever the location of the problem, a constituent that will be directed to the site is chosen as the carrier. The selenium is introduced into an antibody or other site directed molecules by chemical modification of existing moieties such as the amino acid serine, to generate the covalent configurations, RSeH, RSeSeR, RSeSeR' or RSe$^-$.

The selenium may be covalently attached to any protein, antibody, hapten or matrix to be used in any immunoassay or competitive binding assay whereby superoxide ($O_2.^-$) or its descendant reactive oxygen species are used as a detection system using chemiluminescence or chemical dyes or molecules which react with $O_2.^-$ or $H_2O_2$ as the reporter of the unknown selenium adduct concentrations.

The selenium compounds may be attached to any solid or stationary matrix such as a cellulose pad, protein pad, other carbohydrate pad, plastic or other polymer matrix or a biocompatable fibrous matrix for the purpose of generating superoxide ($O_2.^-$) and its descendent reactive oxygen species when the matrix is implanted. The device should not be metallic, but may be an organometallic compound or a metal coated with an organo compound to which the selenium compound can attach. The selenium attached to the insoluble matrix inhibits cell growth in the localized area of the matrix due to the localized generation of superoxide.

Diagnostics, as used herein, refers to molecules to which selenium has been attached, which molecules are then specifically bound to another molecule for use in diagnostic testing for the generation and measurement of superoxide radicals. Examples of diagnostic tests with which the Se-carrier conjugates of the present invention are particularly well suited include competitive binding assays, direct binding assays, immunoassays, and histologic assays, such as nitroblue tetrazolium reduction from forming formazan.

Devices, as used herein, refers to stationary support surfaces of materials such as cellulose, plastics, collagen and polymers capable of attachment to selenium. Examples of such devices include prosthetic heart valves, intraocular lens implants, penile implants, catheters, vascular shunts, and other prosthetic implants having a specialized function. For example, the surface of intraocular lens implants are linked to the selenium compound so that, upon implantation, the selenium catalyzes locally the production of superoxides on the surface of the implant. The superoxide reacts with the cell surface to minimize scar formation. A vascular implant, for example, may be coated with the selenium compound so that, upon implantation coagulation of blood at the implant site is inhibited. The surface of these implants provides a matrix for binding of the selenium compound and site specific delivery of selenium. The effect is localized. Further, any selenium that might escape is in amounts too small to be toxic, and is easily metabolized. Superoxide has a very short half life. It will degrade relatively soon, so it will only do considerable damage at the localized site of its generation.

The non-metal element selenium exists in several catalytic and non-catalytic oxidation states, in vitro and in vivo. If present in sufficient concentrations of thiol compounds, selenium compounds such as selenides, $RSe^-$, oxidize thiols, producing superoxide ($O_2.^-$) and other biologically reactive oxygen species. Superoxide and the other produced reactive products, hydrogen peroxide, thiol radicals and other organic free radicals are toxic to biological membranes, molecules and cells. When present in sufficient concentration as the selenoselenide anion, $RSe^-$, selenium can arrest and kill normal cells, cancer cells, bacterial cells, yeast cells and viruses. When organic selenium compounds are covalently attached to any targeting molecule such as a mono- or polyclonal antibody, peptide or polypeptide, hormone, vitamin, drug, or device, such conjugates comprise a new class of pharmaceuticals and devices that produce free radicals. Selenium is uniquely different from other elements that produce free radicals, i.e., iron, copper or cobalt, in that selenium can readily form small adducts replacing sulfur and it covalently combines with carbon and hydrogen compounds. Such selenium labeled adducts of the proper chemistry will remain non-toxic until activated by a thiol and the free radical pharmacology can be molecularly localized by the carrier molecule. This free radical chemistry is also useful for competitive protein binding assays. The free radical chemistry generated by selenium compounds can be detected by chemiluminescence or reduction of dyes by a spectrophotometer providing for quantitation of a compound which binds the antibody, hapten or drug to which selenium is attached and to which it subsequently reacts with thiols.

A series of tests were conducted to covalently attach the selenium compounds to a variety of carriers. Further tests were done to test the ability of the selenium-carrier conjugates to produce superoxides and kill cells, or inhibit cell growth. The temperature range for attachment of selenium compounds to carriers depends on the carrier used, but in general will be between 4° C. to about 37° C., and preferably between about room temperature and 37° C.

EXAMPLE 1

Synthesis of a Cytotoxic Selenium Carrier Antibody

A human erythrocyte antibody (available from Dako corporation) containing 5 mg protein/ml was incubated with a 1500 fold molar excess of $Na_2IO$, in potassium-phosphate buffer at pH 6.0 for 1–2 hrs at about room temperature. To this solution was added 100 μg of glycerol for the removal of excess periodate and, following dialysis, a 200 fold molar excess of selenocystamine-HCl (available from Sigma Chemical Co.) containing a 1:2.2 molar ratio of triethylamine. This method in its generalized procedure is that described by Hurwitz, E., Levey, R., Mason, R., Wilcheck, M., Aron, R. and Sela, M., "The covalent binding of daunomycin and adrionmycin to antibodies with retention of both drug and antibody", *Cancer Research*, vol. 35, pp. 1175–1181 (1975) and Hurwitz, E., "Specific and nonspecific macromolecular-drug conjugates for the improvement of cancer chemotherapy", *Biopolymers*, vol. 22, pp. 557–567 (1983), by O'Shannessy, D. J. and Quarles, R. H., "Labeling of the oligosaccharide moieties of immunoglobulins", *J. Immunologic Methods*, vol. 99, pp. 153–161 (1987) and by Rodwell et al., U.S. Pat. No. 4,571,958, issued Jun. 9, 1987.

In this reaction the selenocystamine of the configuration (RSeSeR) forms a stable covalent shift base and covalent bond between the selenoamine and the periodate-oxidized carbohydrate aldehyde moiety upon reduction with cyanoborohydride. The antibody-selenium conjugate (Ab-Se) was then separated from the unreacted components upon a column of Shephadex G-25 which was eluted and detected by a UV monitor at 280 nm. Following extensive dialysis, the Ab-Se continuously produced superoxide ($O_2.^-$) at pH 7.2 or pH 9.0 as monitored by lucigenin (available from Sigma Chemical Co.) chemiluminescence, a well known technique, in the presence of glutathione using a Los Alamos Diagnostics Luminometer. Chemiluminescence, which is specific for $O_2.^-$, can be entirely quenched in this reaction by native superoxide dismutase.

EXAMPLE 2

Cytotoxicity of the Ab-Se to Human Erythrocytes

Aliquots of the Ab-Se at various concentrations, i.e., in a dose responsive manner, were incubated at 37° C. for 14 hrs. with a 1% suspension of washed human erythrocytes in a physiologically balanced solution for maintenance of cell viability. At this time erythrocyte hemolysis is measured at 415 nm by absorption of released hemoglobin as described by Hu, M. L. and Spallholz, J. E., "In vitro hemolysis of rat erythrocytes by selenium compounds," *Biochemical Pharmacology*, vol. 32, pp. 957–961 (1983).

EXAMPLE 3

Comparative Examples of Cytotoxicity to Erythrocyte Membrane

In a second measure of cytotoxicity of the Ab-Se conjugate, the following conditions were performed to visually assess cytotoxic damage to the erythrocyte membrane. A 1% suspension of human erythrocytes was incubated at 37° C. for 3 hours with high levels of the Ab-Se carrier prepared as in Example 1. Then the cells were examined for membrane damage using an Olympus Microscope BH with the following optics; 4×, 10×, 40× and 100×.

The experiment consisted of samples of:
1) control erythrocyte cells with no antibody;
2) erythrocyte cells with Ab-Se;
3) erythrocyte cells with native Ab;
4) erythrocyte cells pre-incubated with native Ab for twenty minutes followed by the addition of Ab-Se at 37° C.; and 5) erythrocytes incubated for 3 hrs. at 37° C. with selenocystamine at the same selenium concentration as the Ab-Se, i.e. 0.5 µg Se per Ab-Se conjugate.

The following are descriptions of the appearance of the erythrocyte cells following 3 hours of incubation as followed optically.

1) The control cells all appeared of normal size and shape; they had a typical erythrocyte biconcave disk appearance with a smooth membrane throughout.
2) The erythrocyte cells with Ab-Se revealed extensive lysis by the appearance of cells, with extensive swelling, up to 4–6 times control cell size; the cells also revealed prominent multiple or single membrane holes with extruded cytoplasm; the cells that remained intact revealed extensive burring throughout the membrane with full spike-like edges in appearance, evidence of lipid peroxidation damage to membranes from free radical activity.
3) The erythrocyte cells with the native Ab all appeared of normal size with perfectly smooth cell membranes and no evidence of visual membrane damage; the cells tended to clump together in large arrays of cell masses. This effect is due to the native Ab forming links between cells, i.e., cell-Ab-cell-Ab-cell-Ab, etc. aggregates. There was no lysis of cells.
4) The erythrocyte cells preincubated with native Ab for twenty minutes prior to the addition of Ab-Se appeared identical to #3 above, revealing no cellular membrane damage.
5) The erythrocyte cells incubated with selenocystamine.HCL in equal Se concentrations to Ab-Se showed no lysis of cells yet there appeared to be a small percentage of cells, ca, 5%, with burrs revealing evidence of only minor toxicity to membranes.

This example demonstrates that the Ab alone causes no damage to the cells and that the selenium compound alone, without conjugation to the carrier, causes little or no damage to the cells. When attached to the carrier, as in the Ab-Se, however, the combination causes extensive cell damage. The example in which the cells were preincubated with Ab-Se must specifically bind to the target site to react with thiols and generate superoxide. The preincubation step allows the native Ab to block the binding sites. Low levels of native Ab will inhibit the Ab-Se binding. Higher levels of native Ab will stop Ab-Se binding completely.

FIG. 1 shows that for the same series of comparative tests as those of Example 2, high levels of Ab-Se produced nearly 100% hemolysis at 14 hours, 85% occurring within the first four hours; whereas in the Ab/Ab-Se example having a ratio of 1:1 native Ab to Ab-Se an equal amount of unlabeled native antibody blocked the binding site of the Ab-Se causing a 70% reduction in hemolysis. When the ratio of native Ab to Ab-Se was increased to 2.5:1, the percent hemolysis decreased dramatically. Control cells in PBS and in the presence of native antibody alone exhibited only ca. 8% and 6% spontaneous hemolysis, respectively.

EXAMPLE 4

Synthesis of a Selenium Containing Cytotoxic Cancer Antibody B72.3

An immunoglobulin specific for a widely expressed cancer antigen, TAG-72, originally obtained from colorectal cancer cells, but found in a wide variety of other cancers, has been modified by the covalent attachment of selenocystamine and shown to produce superoxide in the presence of thiol in vitro and bind and be cytotoxic to cancer cells in vitro. In general, 5 mg/ml B72.3 antibody specific to the TAG-72 antigen, produced by well known means in a mouse, is oxidized with 0.42 mg of $NaIO_4$ for 1 hour at 0° C. 100 µl of glycerol is then added. The oxidized B72.3 antibody is reacted with a 200 fold excess of selenocystamine at 4° C. for 48 hours. The antibody-Se complex is then reduced by 100 fold excess of cyanoborohydride and then chromatographed on a G-25 Sephadex column by known techniques. The antibody monitored at 280 nm is collected, dialyzed and concentrated on a Protein G column. The antibody-Se immunoconjugate is shown to produce superoxide ($O_2.^-$) in vitro using amplified lucigenin-chemiluminescence. The chemiluminescence can be inhibited by addition of superoxide dismutase.

Figure 2:
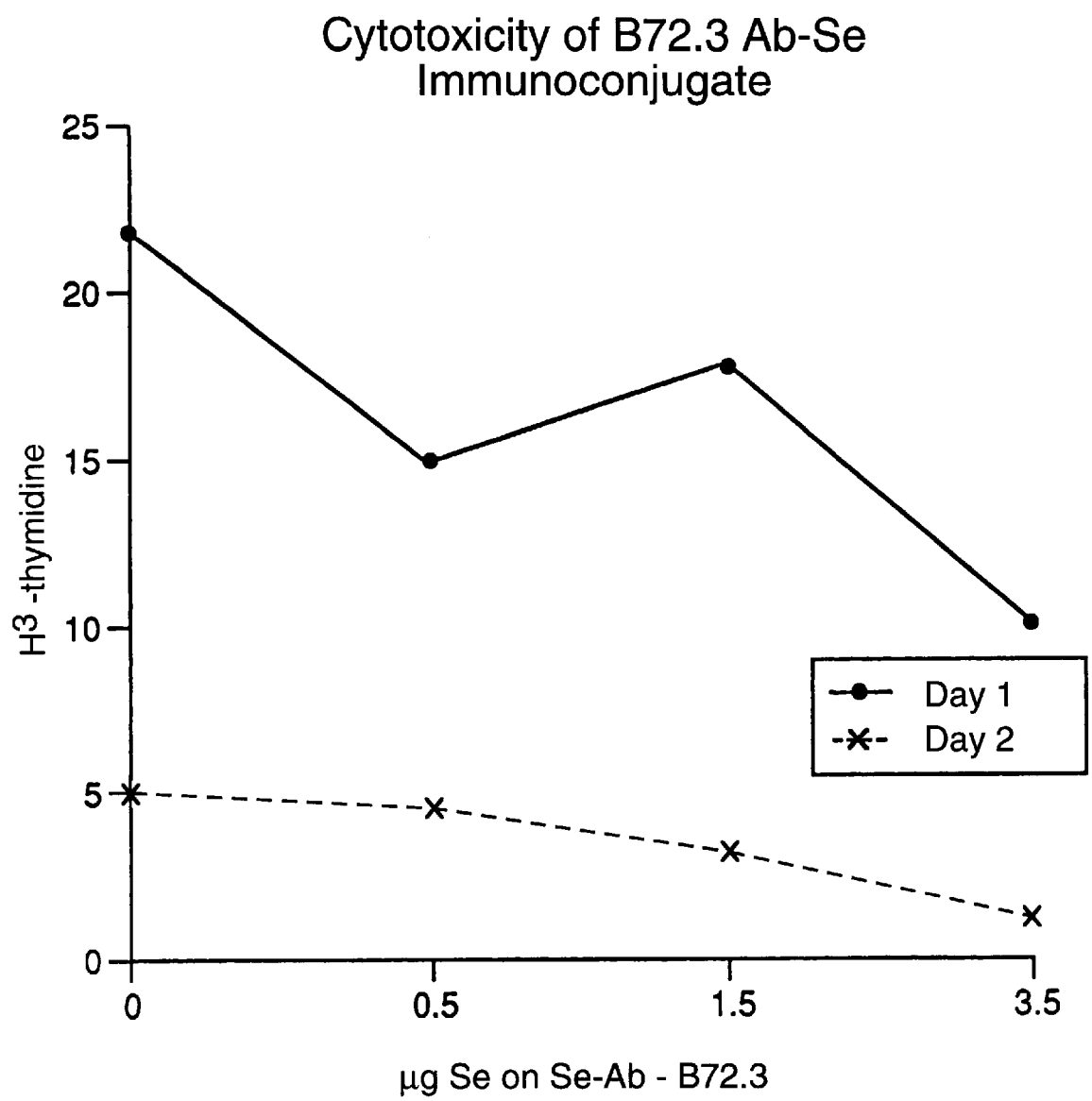
FIG. 2 is a graph showing the cytotoxicity of a covalent antibody-selenium conjugate.

When this cancer antibody is added to cancer cells grown in tissue cultures in 24 well plates, the antibody-Se immunocomplex is shown to be cytotoxic to the cancer cells grown in cultures done in a dose dependent manner over two days and shown in FIG. 2 as measured by cellular incorporation of tritiated thymidine.

EXAMPLE 5

Cytotoxicity of Selenofolate

Another example of this technology is the synthesis of selenofolate from the vitamin, folic acid and selenocystamine.HCl of the configuration, Folate-SeSeR. Into a round bottom flask with stoppers and a stir bar is added 26 mg of selenocystamine.HCl, 44 mg of folic acid and 26 µl of triethylamine in dry (20 ml) chloroform. To this suspension was added 23 mg of dicyclohexylcarbodiimide. The mixture was magnetically stirred for 48 hours after which 4 ml of water was added. The reaction mixture was transferred to a 250 ml round bottom flask and dried using a Buchii 1 rotoevaporator. The dry yellow-orange content was washed with distilled water, which was discarded, and then redissolved in warm methanol. The contents in three aliquots was chromatographed on a 28.0×2.4 cm column of Sephadex LH-20 in methanol. The product, selenofolate was collected between elution volume 71-104 ml. Unlike folic acid, selenofolate is not fluorescent under black (UV) light. The product (very pale yellow-white crystals) was crystallized from hot methanol. The Rf of selenofolate in methanol on 60 Å silica gel TLC is 0.65; the Rf of folic acid and selenocystamine is 0.00. Spectral data in 100% methanol for the product, selenofolate, and the reactants are given in Table 2.

TABLE 2

SPECTRAL DATA OF SELENOFOLATE AND REACTANTS

| | Color | Maximum Absorption | Minimum Absorption |
|---|---|---|---|
| Folic Acid | Bright Yellow | 286 nm 348 nm | 251 nm |
| Selenocystamine .HCL | Bright Yellow | 302 nm | 265 nm |
| Selenofolate | Very Pale Yellow | 276 nm | 259 nm |

The product, selenofolate of the configuration Folate-N—$CH_2CH_2SeSeCH_2CH_2NH_2$, produces superoxide ($O_2.^-$) in the presence of glutathione as measured by lucigenin chemiluminescence. This modified vitamin compound is cytotoxic to cells upon uptake in a dose dependant manner. Derivatives of folate are commonly used chemotherapeutic drugs, as described in Stokstad, E. L. R. and Jukes, T. H. "Sulfonamides and folic acid antagonists: A historical review", J. Nutrition, vol. 117, pp. 1335–1341 (1987); Kramer, K. G., Bell, R. and Pieteraz, G. A., "Aminopterin-Monoclonal antibody conjugates: Antitumor activity and toxicity", Drug Delivery, vol. 1, pp. 29–33 (1993).

EXAMPLE 6
Attachment of Selenocystamine: HCl to a Cellulose Matrix Device

Into a screw-topped 50 ml test tube is added 10 pieces of a cellulose pad of approximately 6 mg each and 34 mg of $Na_2IO_4$ adjusted to pH 6.0 in 20 ml. Periodate oxidation is carried out at room temperature for 4 hrs after which the cellulose pads are drained and washed 5 times with pH 6.0 buffer. To the cellulose pads in 25 ml of PBS buffer pH 6.0 is added 21 mg of selenocystamine.HCl and 30 µl of triethylamine contained in 5 ml of buffer. Beginning at 0 time (control), ½, 1, 2, 3, 4, and 8 hours thereafter, a cellulose pad was removed from the buffer, washed with distilled water and air-dried. Three pads were collected at 8 hrs., washed and air-dried. As shown in Table 3, the capacity of the cellulose pad, cellulose-NH—$CH_2CH_2SeSeCH_2CH_2NH_2$, to generate superoxide ($O_2.^-$) as measured by lucigenin chemiluminescence at pH 7.2 in the presence of glutathione is generally proportional to the incubation time of the oxidized cellulose pad with the selenocystamine.

TABLE 3

CHEMILUMINESCENCE OF
SELENOCYSTANINE LABELED CELLULOSE PADS

| Time of Reaction (hrs.) | Avg. CL units mg Cellulose/Min |
|---|---|
| 0 | 0 |
| 0.5 | 251 |
| 1.0 | 320 |
| 2.0 | 459 |
| 3.0 | 443 |
| 4.0 | 427 |
| 8.0 | 510 |

Additional results demonstrate that the selenium continues to work, without significant variation over time.

Figure 5:
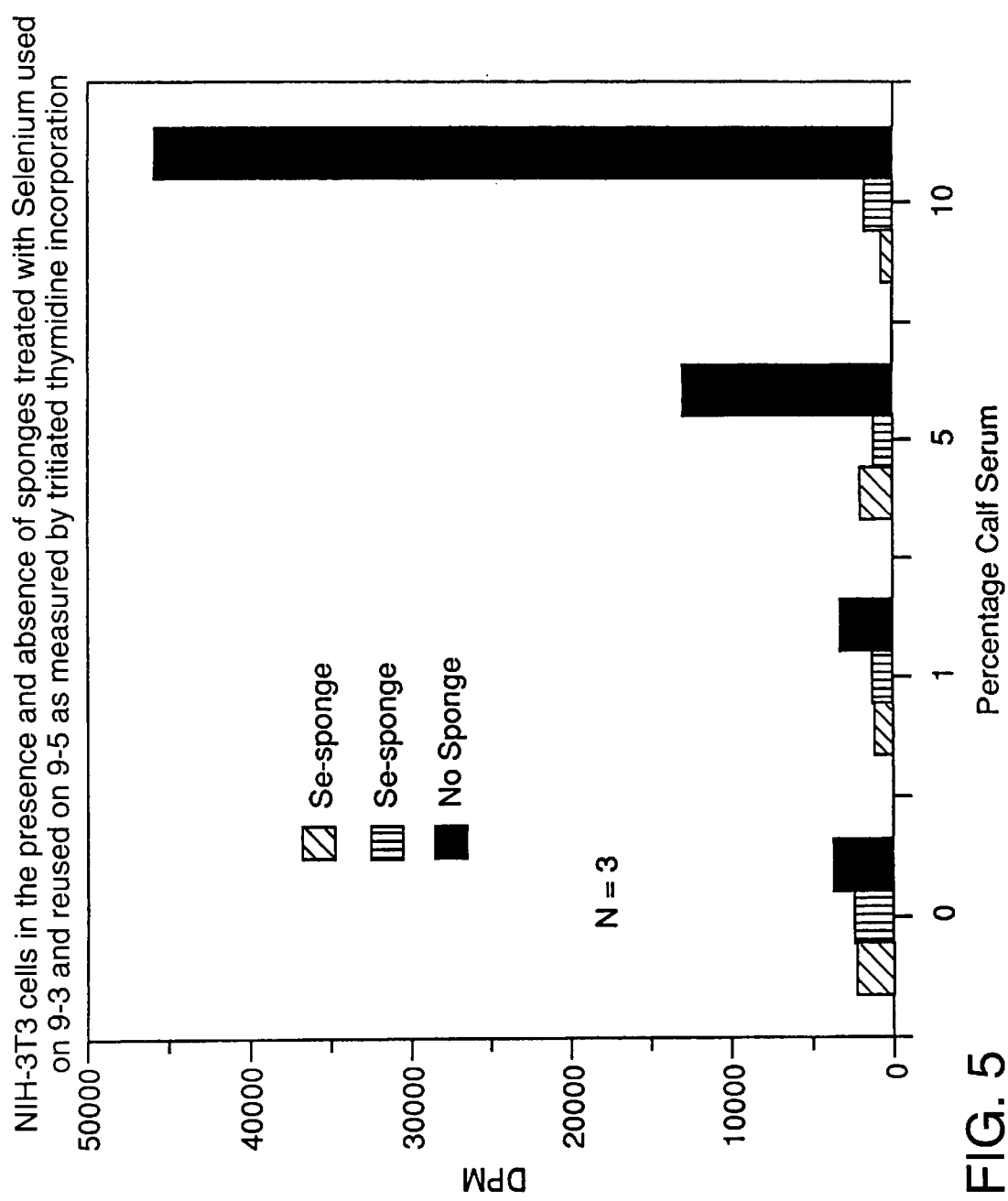
FIG. 5 is a bar graph showing cell growth in the presence and absence of covalently attached selenium treated cellulose sponges as measured by tritiated thymidine incorporation.

FIG. 5 demonstrates the ability of the selenium compounds, when bound to a cellulose sponge, to significantly inhibit the growth of the otherwise fast growing mouse fibroblast cell line, NIH-3T3. The NIH-3T3 cells were grown in plates of calf serum, a standard mixture for stimulating growth. To these plates, sponges prepared as in Example 6 were placed. The experiment was run twice. Each time, cell growth was significantly reduced compared to the control cells not exposed to the selenium-carrier conjugate.

The highest labeled cellulose-selenium pad has been experimentally implanted into the eye of a New Zealand rabbit undergoing primary filtration surgery that mimics human refractory glaucoma. Trabeculectomy failure due to refractory glaucoma is due to fibrosis and scarring of the bleb (a pocket created when tissue sewn back after the opening is made in the anterior chamber of the eye) at the episcleral level. In rabbits, implantation of a piece of the selenium-labeled cellulose pad of ca. 1×0.5 nm under the bleb in comparison to control surgery (a sham operation wherein a cellulose pad not labeled with selenium is implanted in the left eye vs. implantation of the selenium coated cellulose pad in the right experimental eye) has shown the following experimental effects; 1) the experimental eye intravascular pressure was significantly reduced following surgery and took a longer time to return to normal then the control eye, and 2) the experimental eye with the Se-cellulose pad upon pathological examination showed no fibrosis near and within the pad as compared to the control eye with a cellulose pad (no selenium) which had fibrosis. These results show that the cellulose-selenium labeled pad prevents scarring due to fibrosis in rabbits. Scarring due to fibrosis is the main cause of surgical failure in human refractory glaucoma. The cellulose-selenium pad prevented localized formation of scar tissue growth in the rabbits tested without pathological observable damage to normal tissues.

Figure 3:
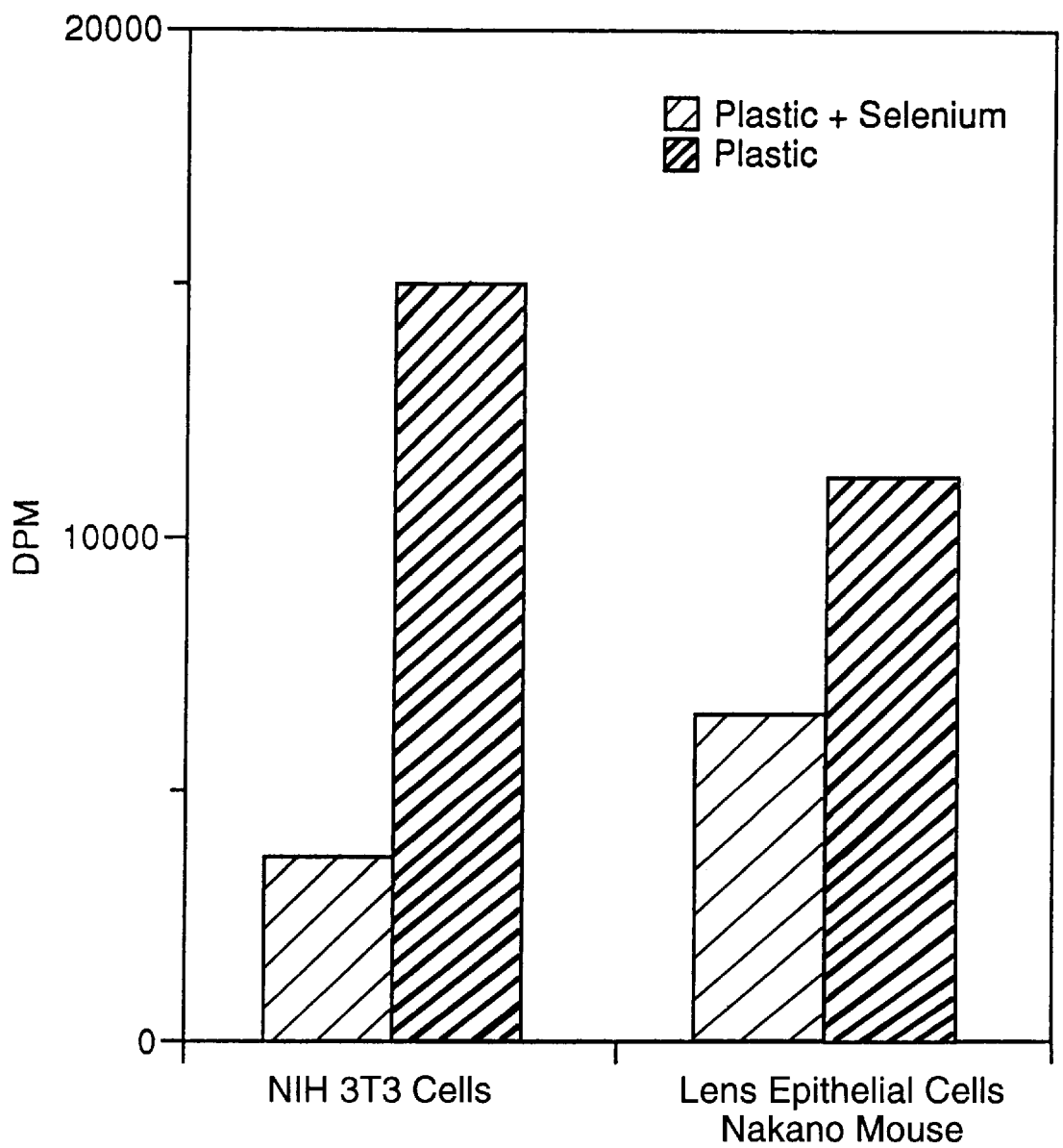
FIG. 3 is a bar graph showing cell growth, as measured by tritiated thymidine incorporation, on plastic treated with $CO_2$ plasma with and without subsequent covalent selenocystamine coupling.
Figure 4:
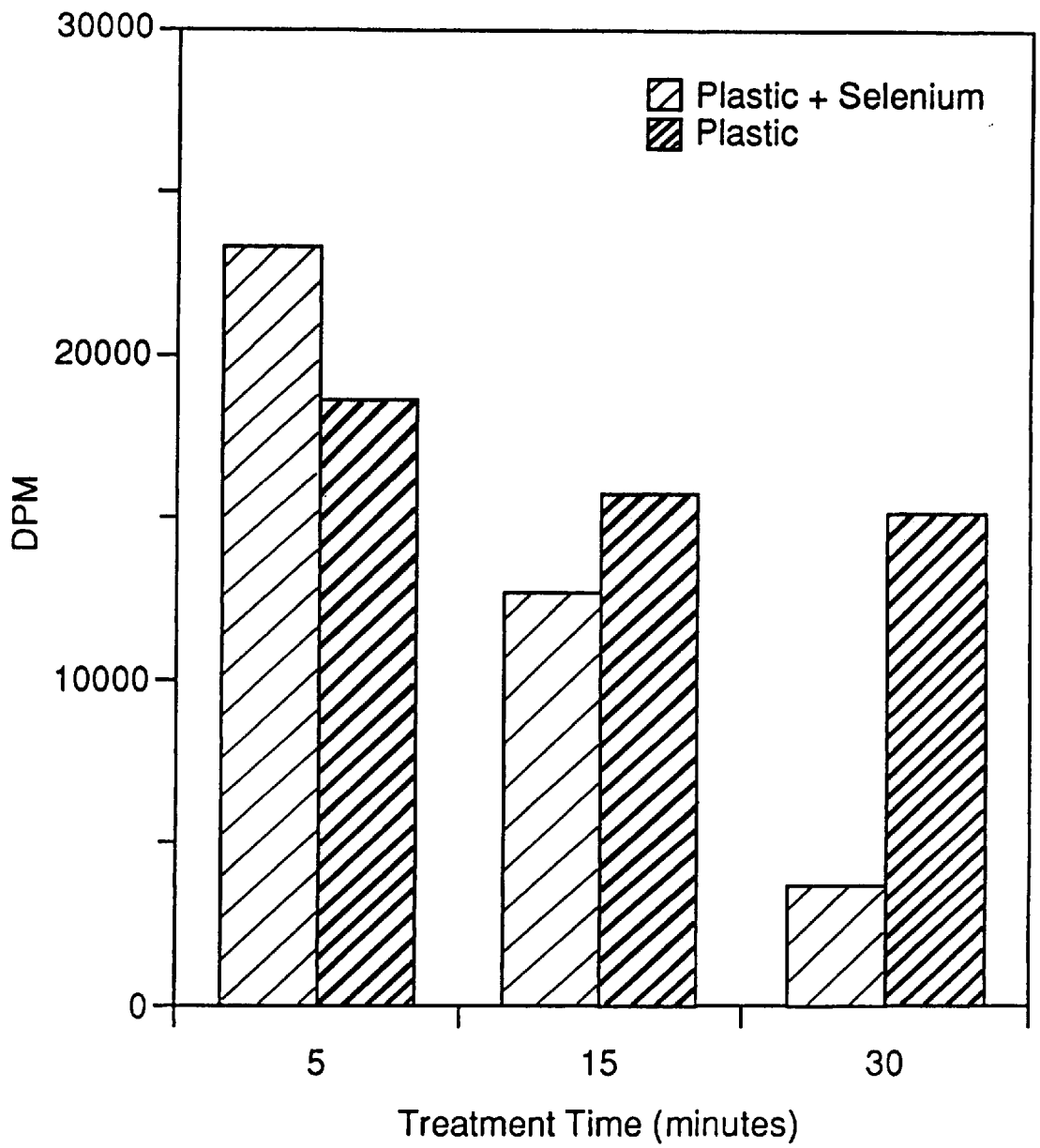
FIG. 4 is a bar graph showing the growth of cells on plastic treated with $CO_2$ plasma with and without subsequent covalent coupling of selenocystamine for varying treatment times.

EXAMPLE 7
Attachment of Selenium Containing Compounds to Plastic Results in a Material That Inhibits Cellular Growth Plastic is treated with an ion flux of $CO_2$ plasma in a gas plasma machine produced by Advanced Plasma Systems, Inc. (St. Petersburg, Fla.). This causes the $CO_2$ to react with the surface layer of atoms to produce carboxyl groups on the surface of the plastic. These carboxyl groups can then be covalently crosslinked by well known techniques, such as those used for peptide synthesis coupling amino groups to a carboxyl group, to selenium containing compounds such as selenocystamine by the use of 1,ethyl-3-(3-dimethylaminopropyl)-carbodiimide hydrochloride. This technique will work for any plastic material including teflon. The plastic containing the covalently attached selenium compound is found to inhibit the growth of cells growing in tissue culture. These results can be seen in FIGS. 3 and 4 where untreated plastic is shown to sustain the growth of cells while the plastic with the selenium attached is shown to inhibit cellular growth.

EXAMPLE 8
Synthesis of the CD-4 Selenopeptide

The HIV virus, which causes AIDS, is known to attach to and destroy the function of helper-T-cells, thereby undermining the immune system. The peptide which represents the segment of the CD4 protein on the surface of helper-T-cells to which the HIV (AIDS) virus attaches, TYICEVEDQKEE, was synthesized. This was modified for better binding to the AIDS virus resulting in the benzylated form: $TYIC_{bzl}E_{bzl}VEDQKEE$. Selenoproprionic acid was then activated by reaction with a carbodiimide, such as EDC[1-ethyl-3-(3-dimethylaminopropyl)-carbodiimide]. This active O-acylisourea intermediate was then reacted with the above peptide to form an adduct that would target the selenium for the AIDS virus.

Tests are underway to demonstrate that the peptide-Se conjugate will specifically bind to the outer surface of the HIV virus, catalyze the production of superoxide upon contact with thiols on the surface proteins of the virus and kill the virus. As stated previously, the mechanism of this invention eliminates the problems encountered due to the lack of an uptake mechanism in viruses. It is hoped that this procedure will also avoid the problems associated with the HIV viruses' ability to mutate and thereby confound previous attempts at killing the virus or treating AIDS.

EXAMPLE 9

Free Radical Diagnostic Applications

Selenium is particularly adapted and has great compatibility with various biochemicals as shown above for the labeling of antibody and folate in Examples 1 and 5, respectively. It is known that free radicals are cytotoxic. The application of this newly described chemistry for selenium conjugates, i.e., the generation of superoxide $O_2.^-$ in the presence of thiols allows for detection limits of $10^{-10}$ to $10^{-12}$ grams per millimeter by chemiluminescence or by reduction of a dye, such as, methylene blue. As stated above, methylene blue and cytochrome C in the oxidized form may be reduced by selenium attached to a receptor molecule, through the generation of superoxide. The amount of reduced methylene blue or cytochrome C can be measured spectrophotometrically and quantitated, thereby reflecting the concentration of the molecule to which selenium is attached.

The present invention improves upon the invention set forth in U.S. Pat. No. 4,341,757 in that 1) no chemical degradation of the selenium containing conjugate is required for analysis, and 2) that the chemiluminescence or dye detection method extends the analytical sensitivity to $10^{-10}$ to $10^{-12}$ grams per millimeter as time amplifies the low concentration of selenium for detection owing to its catalytic nature. U.S. Pat. No. 4,341,757 disclosed classes of selenium compounds which have a high reactivity for proteins, polypeptides and antigens and described the procedure for competitive protein binding assays using a "cold" non-isotopic immunoassay. The present invention extends the detection limits and simplifies the chemistry for stable selenium isotopic immunoassays.

While several theories exist why selenium is carcinostatic and cytotoxic to all cell in vitro and systemically toxic to animals in vivo, only recently has Spallholz, J. E., "On the nature of selenium toxicity and carcinostatic activity," *Free Radical Biology and Medicine*, vol. 17, pp. 45–64, (1994) provided a comprehensive experimental and theoretical understanding of selenium toxicity as a preoxidative catalytic generator of superoxide ($O_2.^-$) and other reactive oxygen descendants. No publication prior to Yan and Spallholz, "Generation of Reactive Oxygen Species From the Reaction of Selenium Compounds With Thiols and Mammary Tumor cells", *Biochemical Pharmacology*, vol. 45, pp. 429–437 (1993) has discussed this free radical chemistry of the simple selenium compounds in the presence of cancer cells.

The understanding and application of this catalytic free radical selenium chemistry by covalent conjugates of only certain configurations of selenium compounds, RSeH, RSeSeR, and RSeSeR' which is targeted to membranes by conjugation, such as monoclonal and polyclonal antibodies, peptides and other molecules such as folate and devices such as a cellulose pad or plastic implant, provides for a targeted selenium toxicity that occurs only in a macromolecular environment without systemic selenium toxicity. Those skilled in the art familiar with targeting molecules (as described in Sela, M. and Hurwitz, E., "Conjugates of antibodies with cytotoxic drugs", *Immunoconjugates, Antibody Conjugates in Radioimaging and Therapy of Cancer*, pp. 189–216 (C-W Vogel, ed.)(Oxford University Press (1987); Dillman et al., "Comparisons of Drug and toxin immunoconjugates", *Antibody, Immunoconjugates and Radiopharmaceuticals*, vol. 1, pp. 65–77 (1988); and, Koppel, G. A., "Recent advances with monoclonal antibody drug targeting for the treatment of human cancer", *Bioconjugate Chemistry*, vol. 1, pp. 13–23 (1990)), such as molecular conjugates of antibodies, peptides, vitamins, liposomes or other targeting agents, will appreciate the pharmacological importance of this targeting selenium free radical technology.

This invention employs the full understanding of the free radical chemistry of specific selenium compounds. While these compounds are systemically toxic this invention utilizes this toxicity in a controlled manner by attaching the selenium compound to a targeting molecule such as an antibody, a binding protein or peptide, or a matrix such as cellulose or plastic. This allows for the selective destruction or inhibition of cellular growth without systemic toxicity. For example we find that the selenium-antibody immunoconjugate is only toxic when it is bound to the cell. This was shown by the fact that when its binding site is occupied by the native antibody no selenium toxicity resulted. We also find that this selenium-antibody conjugate can cause its toxicity from the outside of the cell. In contrast, the non-covalently attached selenium must enter cells to cause toxicity and it can do this to any cancer or normal cell. This insight into the mechanism of selenium toxicity (a selenium-conjugate bound to the outside of a cell is toxic and a selenium-conjugate not able to attach to a cell is not toxic) is novel and allows us to design selenium conjugates that are also toxic to viruses.

What is claimed is:

1. A pharmaceutical agent for the treatment of cancer tumors and pathogenic infections comprising:

a selenium-carrier conjugate for localized delivery and attachment to a target site comprising cancer tumors and pathogens having endogenous thiol compounds, wherein said selenium-carrier conjugate comprises (i) an organic selenium compound selected from the group consisting or RseH, RseR, RseR', RseSeR and RseSeR', wherein R and R' are the same or different and each is an aliphatic residue containing at least one reactive group selected from the group consisting of aldehyde, amino, alcoholic, phosphate, sulfate, halogen or phenolic reactive groups and combinations thereof, covalently attached to (ii) a carrier having a constituent which forms a covalent bond with said reactive groups of said selenium compound to produce said selenium-carrier conjugate, said carrier attaches to said target site for the localized generation of superoxide for localized destruction of pathogens or tumors at said target site; wherein said carrier comprises monoclonal antibodies, polyclonal antibodies, polypeptides, peptides, carbohydrates, lipids, vitamins, drugs, lectin, plasmid, liposome, nucleic acids and implantable devices.

2. The agent recited in claim 1 wherein said pathogens comprise viruses, bacteria, protozoa, rickettsia, yeast, mycoplasma and fungi.

3. The agent recited in claim 1 wherein said carrier is a F(Ab⁻)2 fragment of an antibody specific to the target site.

* * * * *

UNITED STATES PATENT AND TRADEMARK OFFICE
CERTIFICATE OF CORRECTION

PATENT NO. : 5,994,151  
APPLICATION NO. : 09/012161  
DATED : November 30, 1999  
INVENTOR(S) : Julian E. Spallholz et al.

It is certified that error appears in the above-identified patent and that said Letters Patent is hereby corrected as shown below:

On the title page: Item [73] Assignee: delete "Richard-James, Inc." Peabody, Mass."

Signed and Sealed this

Twelfth Day of September, 2006

JON W. DUDAS  
*Director of the United States Patent and Trademark Office*